United States Patent
Bhaduri et al.

(10) Patent No.: US 10,874,680 B2
(45) Date of Patent: Dec. 29, 2020

(54) METHOD OF INCREASING RELATIVE ABUNDANCE OF OSCILLOSPIRA

(71) Applicant: TATA CHEMICALS LIMITED, Mumbai (IN)

(72) Inventors: Anirban Bhaduri, Pune (IN); Ashok Kumar Dubey, Pune (IN); Arup Basu, Pune (IN)

(73) Assignee: Tata Chemicals Limited, Mumbai (IN)

( * ) Notice: Subject to any disclaimer, the term of this patent is extended or adjusted under 35 U.S.C. 154(b) by 0 days.

(21) Appl. No.: 16/140,593

(22) Filed: Sep. 25, 2018

(65) Prior Publication Data

US 2019/0091250 A1    Mar. 28, 2019

(30) Foreign Application Priority Data

Sep. 25, 2017 (IN) .............................. 201721034022

(51) Int. Cl.
| | | |
|---|---|---|
| *A61K 31/702* | (2006.01) | |
| *A61K 31/733* | (2006.01) | |
| *A61K 9/00* | (2006.01) | |
| *C12N 1/20* | (2006.01) | |
| *A61K 45/06* | (2006.01) | |

(52) U.S. Cl.
CPC .......... *A61K 31/702* (2013.01); *A61K 9/0053* (2013.01); *A61K 31/733* (2013.01); *A61K 45/06* (2013.01); *C12N 1/20* (2013.01); *A61K 2300/00* (2013.01)

(58) Field of Classification Search
CPC .. A61K 31/702; A61K 31/733; A61K 9/0053; A61K 45/06; A61K 2300/00; C12N 1/20
USPC ......................................................... 514/54
See application file for complete search history.

(56) References Cited

FOREIGN PATENT DOCUMENTS

| JP | 159647 A1 | 9/2017 |
|---|---|---|
| WO | 024638 A2 | 2/2012 |
| WO | 077794 A1 | 5/2015 |
| WO | 153841 A1 | 10/2015 |
| WO | 183535 A1 | 11/2016 |

OTHER PUBLICATIONS

Bouhnik et al. Four-week short chain fructo-oligosaccharides ingestion leads to increasing fecal bifidobacteria and cholesterol excretion in healthy elderly volunteers. Nutrition Journal 2007, 6:42 (7 pages). (Year: 2007).*
Konikoff et al. Oscillospira: a Central, Enigmatic Component of the Human Gut. Trends in Microbiology, Jul. 2016, vol. 24, No. 7, p. 523-524. (Year: 2016).*
Salazar et al. Exopolysaccharides Produced by Intestinal Bifidobacterium Strains Act as Fermentable Substrates for Human Intestinal Bacteria. Applied and Environmental Microbiology, Aug. 2008, vol. 74, No. 15, p. 4737-4745. (Year: 2008).*

* cited by examiner

*Primary Examiner* — Yih-Horng Shiao
(74) *Attorney, Agent, or Firm* — Wood Herron & Evans LLP

(57) ABSTRACT

The present application provides a method of increasing relative abundance of *Oscillospira* in gastro-intestinal tract of a subject. The method comprising administering to said subject at least 2.5 g per day of fructo-oligosaccharide, such that the abundance of *Oscillospira* is increased to a statistically significant level when measured by F-test. A composition for increasing relative abundance of *Oscillospira* in gastro-intestinal tract of a subject is also disclosed.

6 Claims, 7 Drawing Sheets

Figure 13

METHOD OF INCREASING RELATIVE ABUNDANCE OF OSCILLOSPIRA

FIELD OF INVENTION

The present disclosure relates to a method and composition for promoting growth of a bacteria in the gastrointestinal tract of a subject. Specifically, the present disclosure relates a method and composition for increasing the abundance of the bacteria *Oscillospira* in the gastro-intestinal tract of a mammal.

BACKGROUND

The gastro-intestinal tract or gut of a mammal harbours within itself a complex ecosystem that includes several bacterial species. For example, there are approximately 300 to 500 bacterial species in the intestinal tract of a human being (*Quigley EMM. Gut Bacteria in Health and Disease. Gastroenterology & Hepatology.* 2013; 9 (9):560-569). These bacteria are extremely beneficial to the host. For example, these bacteria help in maintaining a healthy gut and increase resistance against pathogenic bacteria.

*Oscillospira* a bacteria of the phylum *Firmicutes* is implicated in weight management and cardiovascular health. It has been reported that based on UniFrac analysis of microbiome communities, *Oscillospira* significantly correlated with lower body mass (rho=−0.71, P=0.0009)(Goodrich et al., 2014). It has been established that *Oscillospira* abundance is associated with visceral fat mass (VFM) and android/gynoid ratio (measures of body fat distribution). Both these measures are directly linked with cardio-vascular health of an individual. It was observed that *Oscillospira* negatively correlated with these measures (Beaumont et al, 2016).

Thus, for certain conditions there is a need for enhancing the population of *Oscillospira* in the gastro-intestinal tract of a mammal especially a human being.

SUMMARY

A method of increasing abundance of *Oscillospira* in gastro-intestinal tract of a subject is provided. The method includes administering to said subject at least 2.5 grams per day of fructo-oligosaccharide, such that the abundance of *Oscillospira* is increased to a statistically significant level when measured by F-test.

A composition for increasing abundance of *Oscillospira* in gastro-intestinal tract of a subject is also provided. The composition comprises at least 2.5 g of fructo-oligosaccharide, wherein said composition promotes an increase in abundance of *Oscillospira* in the gastro-intestinal tract of the subject to a statistically significant level when measured by F-test.

BRIEF DESCRIPTION OF DRAWINGS

FIG. 13 depicts the relative abundance of *Prevotella copri* in fecal samples before and during fructo-oligosaccharide intervention at a dose of 2.5 grams per day.

DETAILED DESCRIPTION

Figure 1:
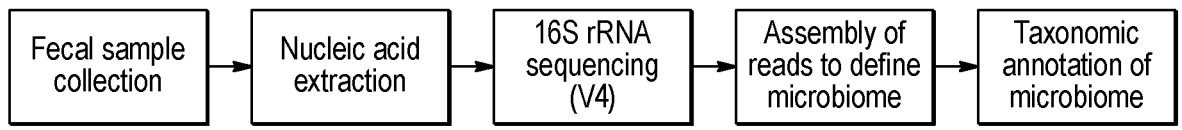
FIG. 1 depicts a sample processing pipeline for microbiome annotation in accordance with an embodiment.

For the purpose of promoting an understanding of the principles of the invention, reference will now be made to embodiments and specific language will be used to describe the same. It will nevertheless be understood that no limitation of the scope of the invention is thereby intended, such alterations and further modifications in the disclosed product and process, and such further applications of the principles of the invention therein being contemplated as would normally occur to one skilled in the art to which the invention relates.

It will be understood by those skilled in the art that the foregoing general description and the following detailed description are exemplary and explanatory and are not intended to be restrictive.

Reference throughout this specification to "one embodiment" "an embodiment" or similar language means that a particular feature, or characteristic described in connection with the embodiment is included in at least one embodiment of the present invention. Thus, appearances of the phrase "in one embodiment", "in an embodiment" and similar language throughout this specification may, but do not necessarily, all refer to the same embodiment.

The present disclosure provides a method of increasing the abundance of bacteria of the genus *Oscillospira* (herein after referred to as *Oscillospira*) in gastro-intestinal tract of a subject. The disclosure also provides a composition for increasing the abundance of *Oscillospira* in gastro-intestinal tract of a subject.

Increase in abundance of *Oscillospira* according to the present disclosure means that at least one species of bacteria belonging to the genus *Oscillospira*, is increased in the gastro-intestinal tract of the subject.

The method of increasing the abundance of *Oscillospira* comprises administering to the subject a composition comprising fructo-oligosaccharide in an amount sufficient to increase the abundance of *Oscillospira* in the gastro-intestinal tract of the subject to a statistically significant level when measured by F-Test.

In accordance with an embodiment, the method results in an increase in absolute abundance of *Oscillospira* in the gastro-intestinal tract of the subject to a statistically significant level when measured by F-Test.

As used herein 'Absolute Abundance' refers to the total count of the bacterium of interest. The total count or abundance of a bacterium may be determined most easily by quantification of the bacterium from a sample. Methods for quantification of bacteria include but are not limited to genomic sequencing, metagenomic sequencing or standard cell culturing methods based on optics.

In accordance with an alternative embodiment, the method results in an increase in relative abundance of *Oscillospira* in the gastro-intestinal tract of the subject to a statistically significant level when measured by F-Test.

As used herein 'Relative Abundance' refers to the count of bacterium of interest divided by the total count of all the measured bacteria, unless otherwise indicated. The relative abundance of a bacterium may be determined most easily by quantification of all bacteria from a sample. Methods for quantification of bacteria include but are not limited to genomic sequencing, metagenomic sequencing or standard cell culturing methods based on optics.

In accordance with an embodiment, statistically significant level refers to a F-score reflective of a P-value less than or equal to 0.05

In accordance with an aspect, the subject is a mammal. In accordance with an embodiment the mammal is a human being.

The amount of composition administered to the subject, is such that a dose of at least 2.5 grams per day of fructo-oligosaccharide is administered to the subject. In accordance with an embodiment, the amount of composition administered is such that the dose of between about 2.5 grams per day to about 10 grams per day of fructo-oligosaccharide is administered to the subject. The daily amount of fructo-oligosaccharide may be administered for at least about 1 day to about 3 months (i.e., about 90 days). However, the daily amount of fructo-oligosaccharide may be administered even for a longer period. The daily amount may be administered once per day or maybe divided into two or three portions that may or may not be equal.

In accordance with an embodiment, the dose of fructo-oligosaccharide required to increase the absolute abundance or relative abundance of *Oscillospira* may be determined based on the initial absolute abundance or relative abundance of *Oscillospira* in the intestine of the subject.

A composition for increasing the abundance of *Oscillospira* in the gastro-intestinal tract of the subject is disclosed. The composition comprising at least 2.5 grams of fructo-oligosaccharide. The composition comprises between 2.5 grams to 10 grams of fructo-oligosaccharide.

In accordance with an aspect, the composition is a mixture of oligosaccharides consisting of a sucrose molecule (glucose-fructose disaccharide, GF1) linked to one (GF2), or two (GF3) or three (GF4) additional fructose units added by β-2-1 glycosidic linkages to the fructose unit of the sucrose. The GF2, GF3, and GF4 oligosaccharides, are also called 1-kestose, nystose and fructofuranosyl nystose, respectively.

In accordance with an embodiment, composition comprises about 40-50% 1-kestose (GF2), 40-50% nystose (GF3) and 5-10% fructofuranosyl nystose (GF4).

The composition may contain other components including but not limited to galacto-oligosaccharides, vitamins, minerals, plant extracts or mixtures thereof. The composition may also contain pharmaceutically acceptable excipients.

The composition may be in any desirable formulation suitable for oral intake. In accordance with an embodiment, the composition is in the form of a solid dosage form or a liquid dosage form. In an example, the composition is in the form of an oral syrup.

EXAMPLES

Experimental Design and Sample Collection

The study was conducted as per the pertinent requirements of the ICMR guidelines for Biomedical Research on Human Subjects, Good Clinical Practices for Clinical Research in India. The protocol was carried out in accordance with the approved guidelines, and was in agreement with Declaration of Helsinki principles.

The study was a random, double blinded design and was performed on a cohort of sixty (60) subjects. The group of sixty healthy adults were randomly divided into three (3) groups: T1 group, T2 group, and T3 group depending upon the amount of fructo-oligosaccharide received/consumed. Table 1, provides the amount of fructo-oligosaccharide that is received/consumed by each group.

| Group | Amount of fructo-oligosaccharide consumed per day |
|---|---|
| T1 | 2.5 grams |
| T2 | 5 grams |
| T3 | 10 grams |

All participants consumed the assigned dosage of fructo-oligosaccharide on daily basis for three (3) months. DNA from the gut bacteria present in the fecal samples of the sixty subjects defining the cohort was extracted. For each of the sixty subjects, samples were collected at seven (7) time points three (3) -time points before the subject received the fructo-oligosaccharide i.e on the $-60^{th}$, $-30^{th}$ and $0^{th}$ day, and four (4) times during the three (3) month during fructo-oligosaccharide intervention i.e., on the $1^{st}$, $30^{th}$, $60^{th}$ and $90^{th}$ day.

Sample Processing

Each fecal sample was processed using standard nucleic acid extraction protocols. After the nucleic acid extraction, 16S rRNA gene based sequencing of the extracted DNA was performed. V4 region of the extracted 16S rRNA gene was amplified and sequenced. Obtained sequenced data was processed using a standard pipeline (using Second Genome pipeline). Post processing through the mentioned pipeline, abundance of *Oscillospira* was computed and tabulated. An exemplary sample processing pipeline for microbiome annotation is shown in FIG. 1.

Data Analytics

Statistical assessment of abundance change of microorganism was performed using F-test. The test was performed on the R platform. Change in relative abundance of *Oscillospira* prior to intervention with fructo-oligosaccharide and during intervention across the arms of the study was assessed and reported.

Results

It is observed that fructo-oligosaccharide was able to increase relative abundance of *Oscillospira*. The study explored relative abundance change for three *Oscillospira* species (*Oscillospira* 97otu17549, *Oscillospira* 97otu18360 and *Oscillospira* unclassified) and increase in relative abundance was observed across all species. Table 1 below provides the F-test statistic (and P-value) to report reduction of *Oscillospira* species in individuals intervened with fructo-oligosaccharide.

TABLE 1

Summary of *Oscillospira* response at multiple dosages reported below.

| Organisms | Dosage (grams per day) | | |
| --- | --- | --- | --- |
| | 2.5 | 5 | 10 |
| *Oscillospira* 97otu17549 | 0.3 (7.5*e−6) | 0.6 (0.06) | 0.5 (0.02) |
| *Oscillospira* 97otu18360 | 1.0 (0.9) | 1.3 (0.27) | 0.2 (1.14*e−7) |
| *Oscillospira* unclassified | 0.4 (6.08*−4) | 1.0 (0.85) | 1.3 (0.3) |

Figure 2:
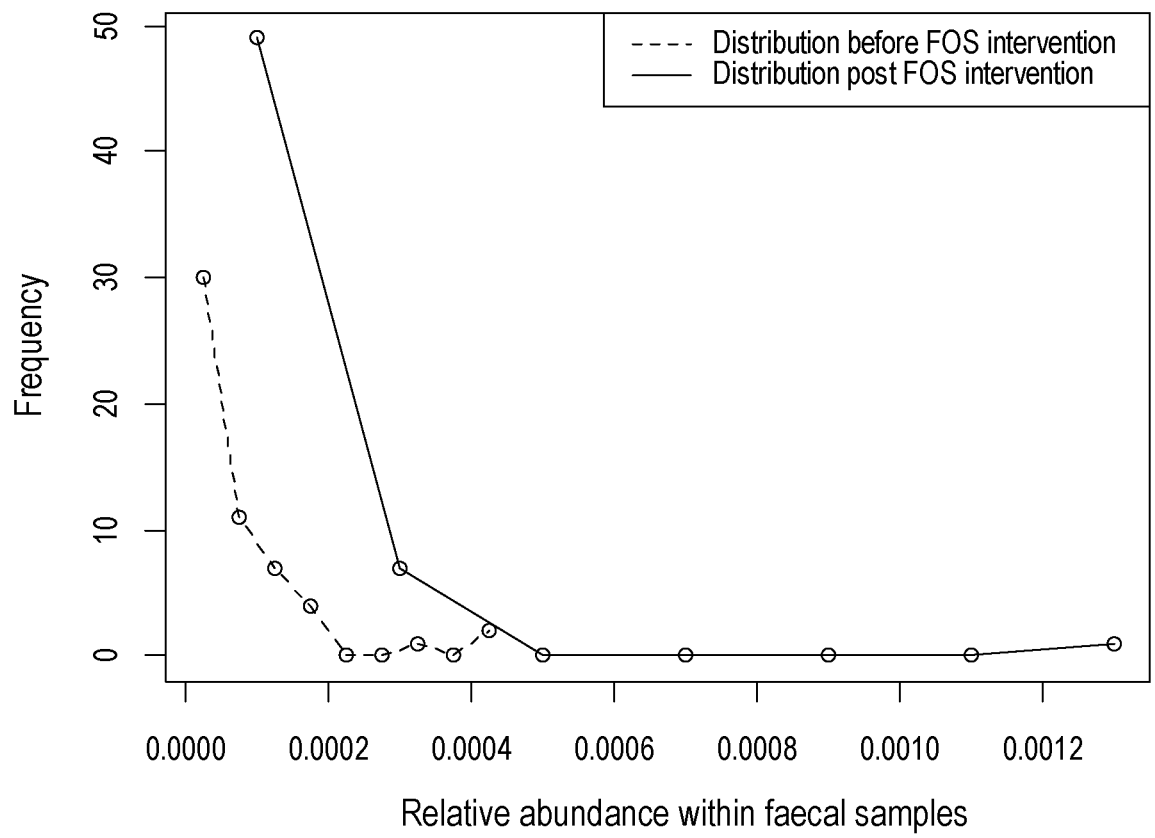
FIG. 2 depicts the distribution of *Oscillospira* 97otu17549 in fecal sample before and during fructo-oligosaccharide intervention at a dose of 2.5 grams of fructo-oligosaccharide per day in accordance with an embodiment.
Figure 3:
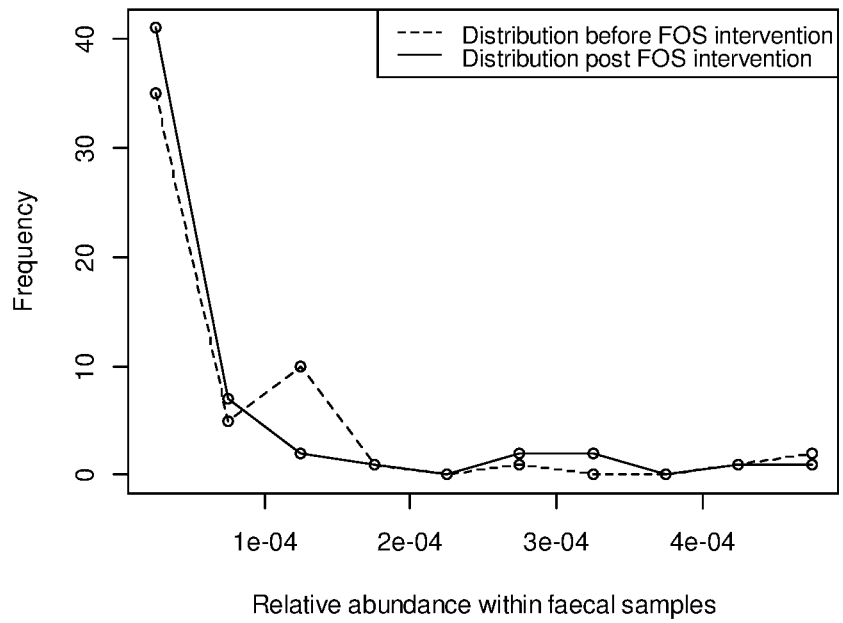
FIG. 3 depicts the distribution of *Oscillospira* 97otu18360 in fecal sample before and during fructo-oligosaccharide intervention at a dose of 2.5 grams of fructo-oligosaccharide per day in accordance with an embodiment.
Figure 4:
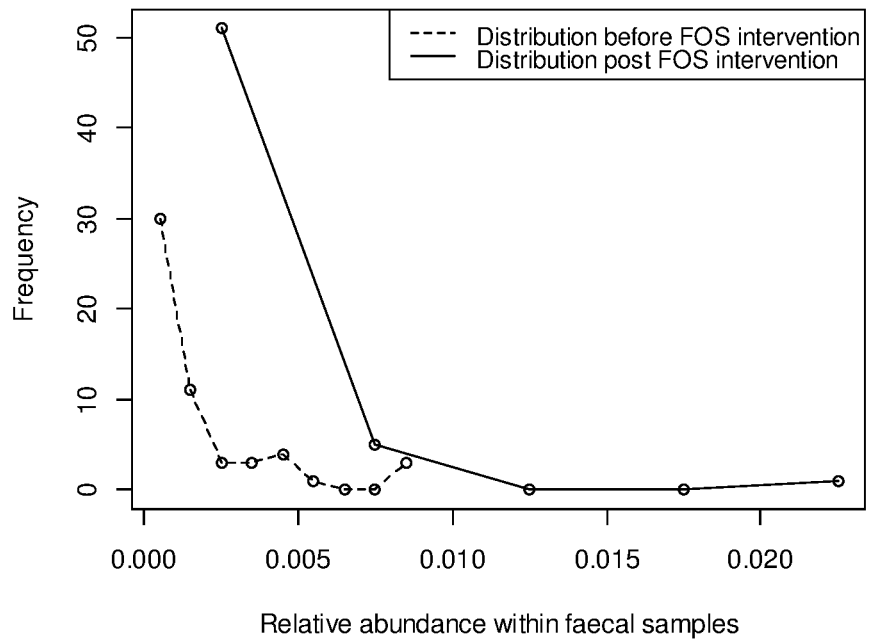
FIG. 4 depicts the distribution of *Oscillospira* 97otu41912 in fecal sample before and during fructo-oligosaccharide intervention at a dose of 2.5 grams of fructo-oligosaccharide per day in accordance with an embodiment.

FIGS. 2-4 reports the relative abundance of different species of *Oscillospira* on intervention with fructo-oligosaccharide. The term frequency refers to the relative occurence or abundance of an organism in a given sample compared to the total population of the complete bacterial population.

However, no change in relative abundance of other bacterium such as *Roseburia hominis, Prevotella copri* and *Bacteroides plebeius* was observed in subjects after intervention of fructo-oligosaccharide. FIGS. 5-13 report the relative abundance of some of these bacteria before and during intervention with fructo-oligosaccharide. The term frequency refers to the relative occurrence or abundance of an organism in a given sample compared to the total population of the complete bacterial population.

Figure 5:
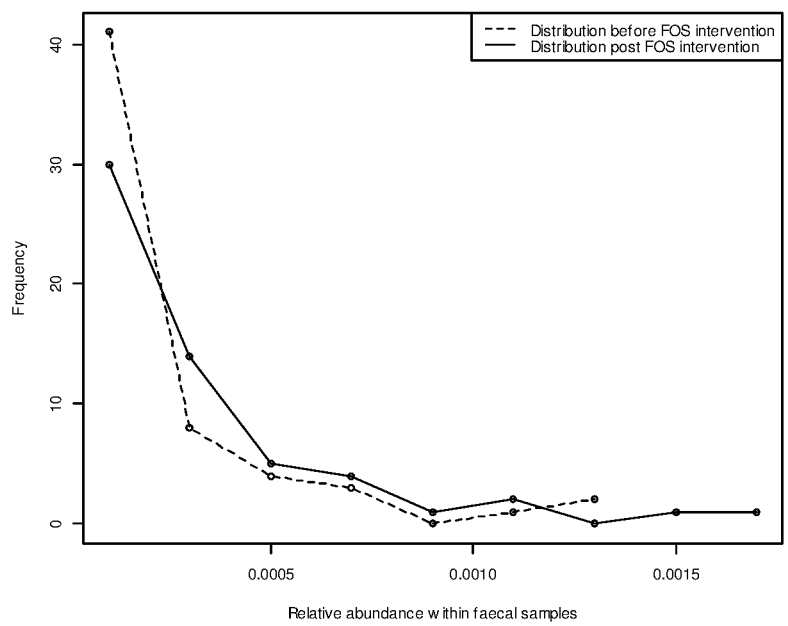
FIG. 5 depicts the relative abundance of *Roseburia hominis* in fecal samples before and during fructo-oligosaccharide intervention at a dose of 10 grams per day.

FIG. 5 depicts the relative abundance of *Roseburia hominis* in fecal samples before and during fructo-oligosaccharide intervention. On intervention of fructo-oligosaccharide at a dose of 10 grams per day, no significant relative abundance change was observed (F-statistics=0.64, P-value=0.09).

Figure 6:
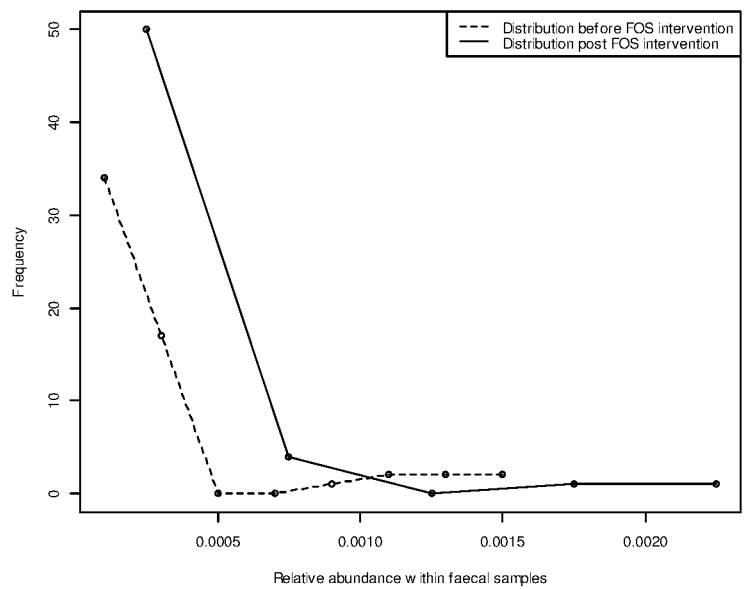
FIG. 6 depicts the relative abundance of *Roseburia hominis* in fecal samples before and during fructo-oligosaccharide intervention at a dose of 5 grams per day.

FIG. 6 depicts the relative abundance of *Roseburia hominis* in fecal samples before and during fructo-oligosaccharide intervention. On intervention of fructo-oligosaccharide at a dose of 5 grams per day, no significant relative abundance change was observed (F-statistics=1.04, P-value=0.87).

Figure 7:
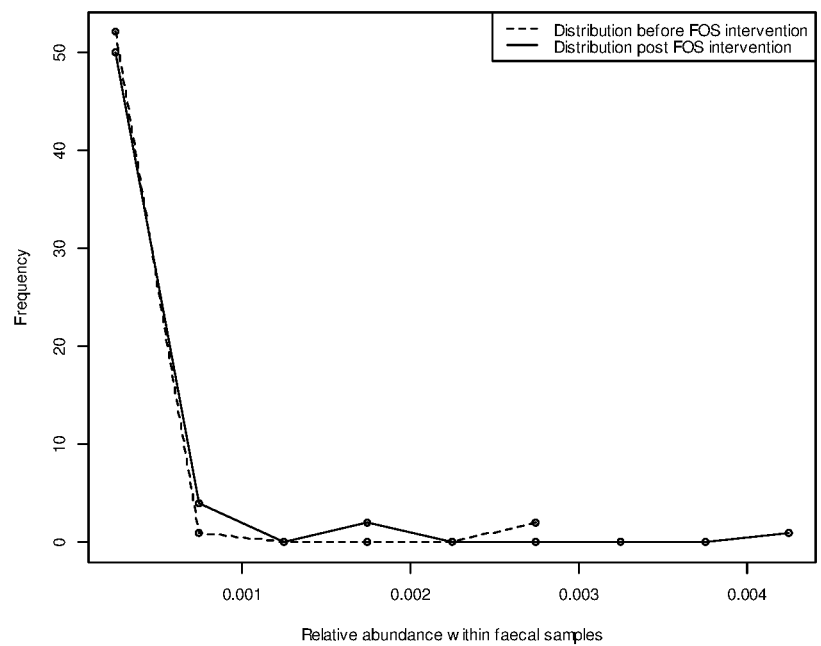
FIG. 7 depicts relative adundance of *Roseburia hominis* in fecal samples before and during fructo-oligosaccharide intervention at a dose of 2.5 grams per day.

FIG. 7 depicts relative abundance of *Roseburia hominis* in fecal samples before and during fructo-oligosaccharide intervention. On intervention of fructo-oligosaccharide at a dose of 2.5 grams per day, no significant relative abundance change was observed (F-statistics=0.64, P-value=0.10).

Figure 8:
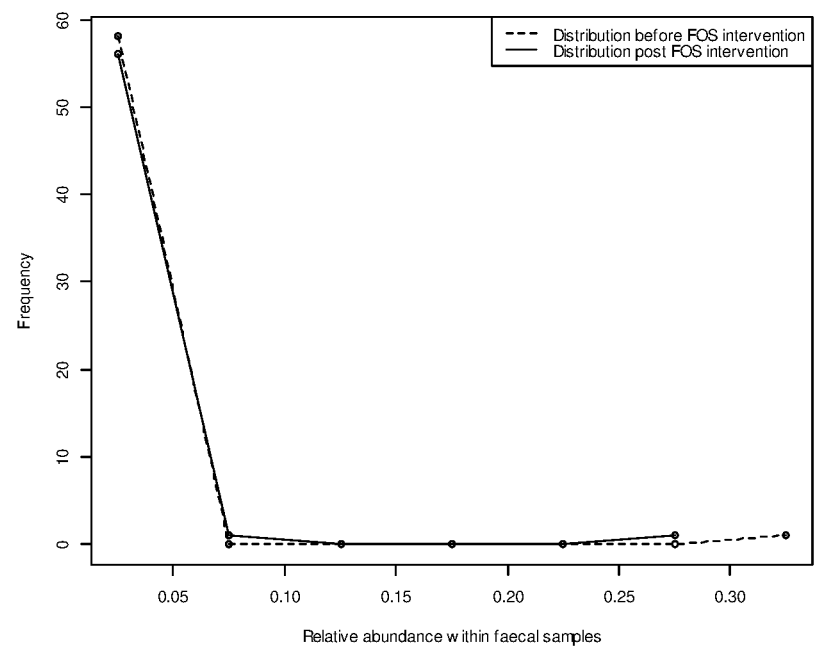
FIG. 8 depicts relative abundance of *Bacteroides plebeius* in fecal samples before and during fructo-oligosaccharide intervention at a dose of 10 grams per day.

FIG. 8 depicts relative abundance of *Bacteroides plebeius* in fecal samples before and during fructo-oligosaccharide intervention. On intervention of fructo-oligosaccharide at a dose of 10 grams per day, no significant relative abundance change was observed (F-statistics=0.86, P-value=0.76).

Figure 9:
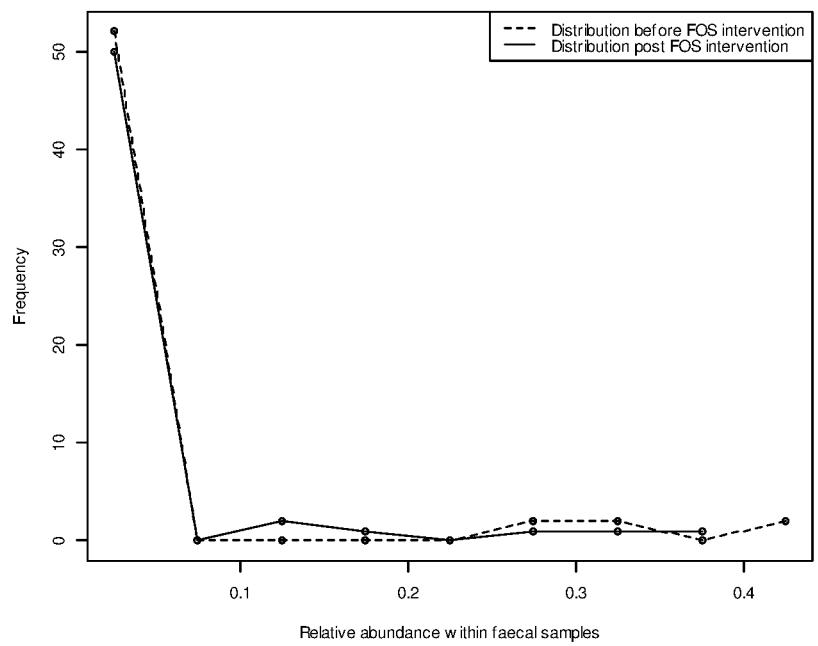
FIG. 9 depicts relative abundance of *Bacteroides plebeius* in fecal samples before and during fructo-oligosaccharide intervention at a dose of 5 grams per day.

FIG. 9 depicts relative abundance of *Bacteroides plebeius* in fecal samples before and during fructo-oligosaccharide intervention. On intervention of fructo-oligosaccharide at a dose of 5 grams per day, no significant relative abundance change was observed (F-statistics=1.69, P-value=0.52).

Figure 10:
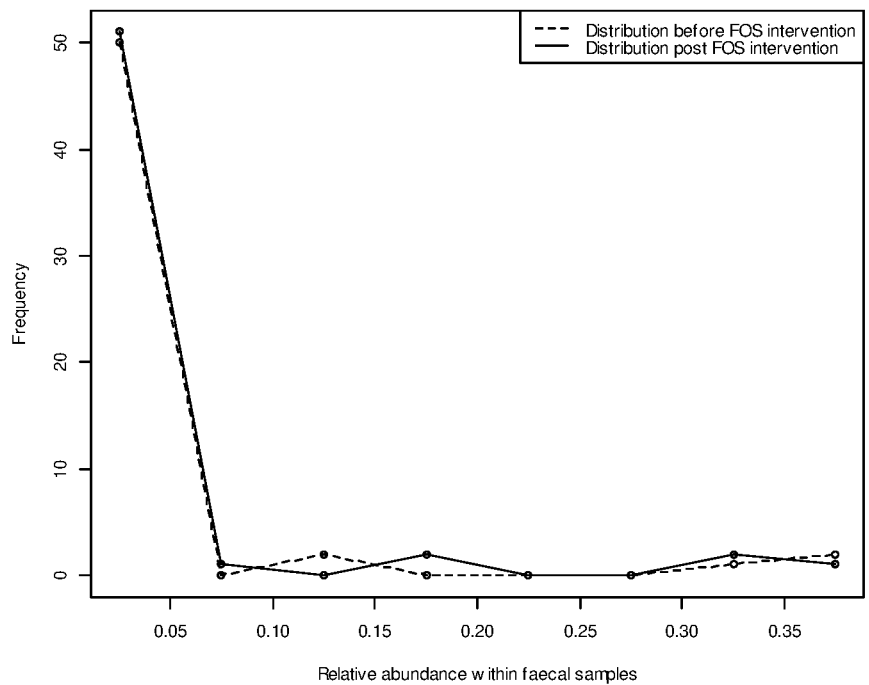
FIG. 10 depicts the relative abundance of *Bacteroides plebeius* in fecal samples before and during fructo-oligosaccharide intervention at a dose of 2.5 grams per day.

FIG. 10 depicts the relative abundance of Bacteroides plebeius in fecal samples before and during fructo-oligosaccharide intervention. On intervention of fructo-oligosaccharide at a dose of 2.5 grams per day, no significant relative abundance change was observed (F-statistics=1.1, P-value=0.71).

Figure 11:
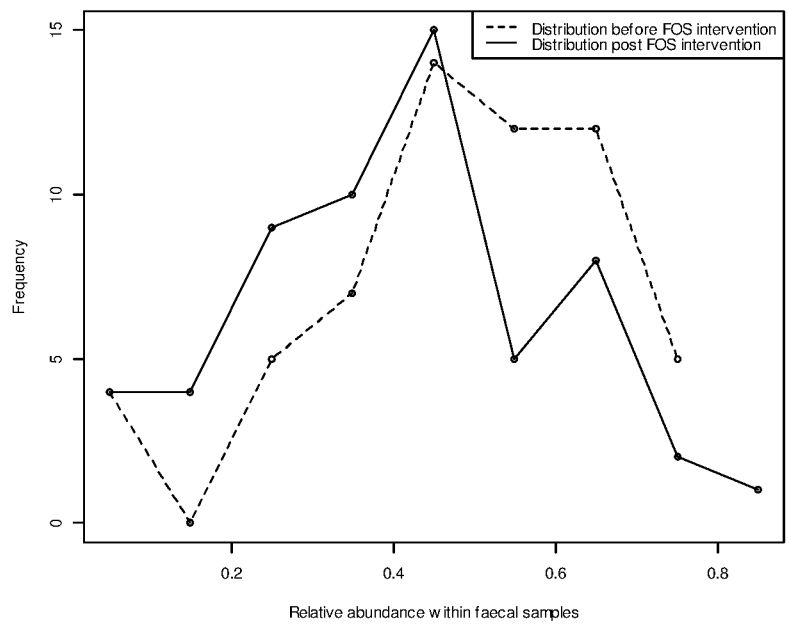
FIG. 11 depicts the relative abundance of *Prevotella copri* in fecal samples before and during fructo-oligosaccharide intervention at a dose of 10 grams per day.

FIG. 11 depicts the relative abundance of *Prevotella copri* in fecal samples before and during fructo-oligosaccharide intervention. On intervention of fructo-oligosaccharide at a dose of 10 grams per day, no significant relative abundance change was observed (F-statistics=0.95, P-value=0.84).

Figure 12:
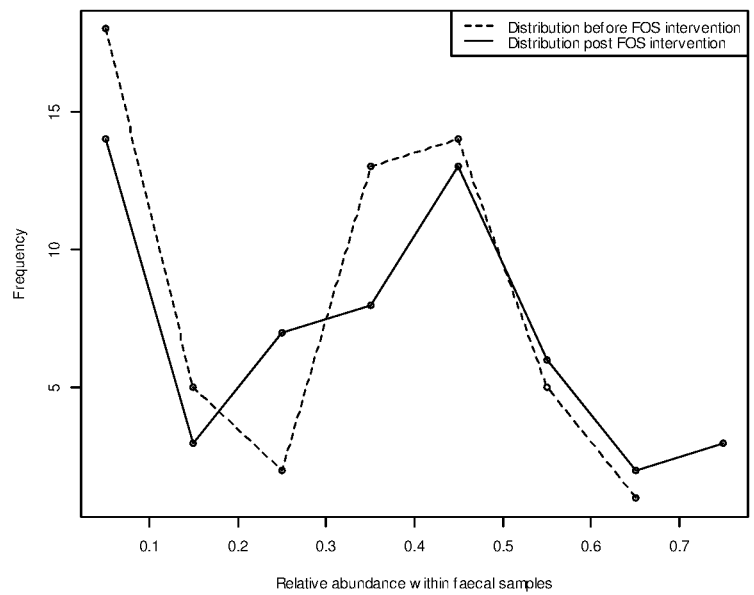
FIG. 12 depicts the relative abundance of *Prevotella copri* in fecal samples before and during fructo-oligosaccharide intervention at a dose of 5 grams per day.

FIG. 12 depicts the relative abundance of *Prevotella copri* in fecal samples before and during fructo-oligosaccharide intervention. On intervention of fructo-oligosaccharide at a dose of 5 grams per day, no significant relative abundance change was observed (F-statistics=0.82, P-value=0.44).

Figure 13:
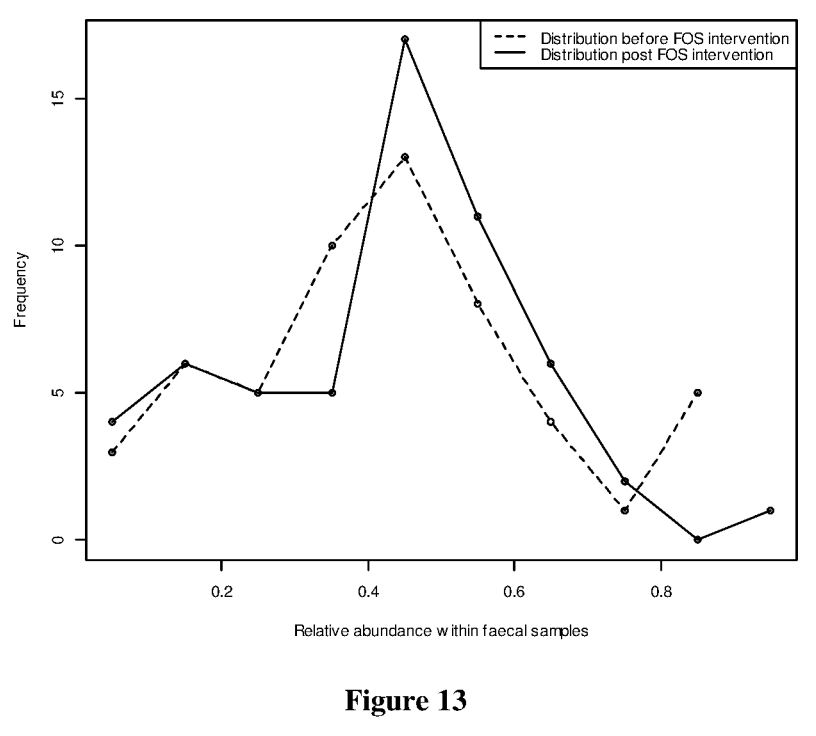

FIG. 13 depicts the relative abundance of *Prevotella copri* in fecal samples before and during fructo-oligosaccharide intervention. On intervention of fructo-oligosaccharide at a dose of 2.5 grams per day, no significant relative abundance change was observed (F-statistics=1.07 P-value=0.78).

SPECIFIC EMBODIMENTS

A method of increasing relative abundance of *Oscillospira* in gastro-intestinal tract of a subject is disclosed. The method comprising administering to said subject at least 2.5 grams per day of fructo-oligosaccharide, such that the abundance of *Oscillospira* is increased to a statistically significant level when measured by F-test.

Such a method, wherein 2.5 grams per day to 10 grams per day of fructo-oligosaccharide is administered to said subject.

Such a method, wherein the subject is a mammal and preferably the subject is a human being.

Such a method, wherein the fructo-oligosaccharide is administered for 1 day to 90 days.

Such a method, wherein the fructo-oligosaccharide administered comprise about 40-50% 1-kestose(GF2), 40-50% nystose(GF3) and 5-10% fructofuranosyl nystose (GF4).

A composition for increasing relative abundance of *Oscillospira* in gastro-intestinal tract of a subject is disclosed. The composition comprising at least 2.5 grams of fructo-oligosaccharide, wherein said composition promotes an increase in abundance of *Oscillospira* in the gastro-intestinal tract of the subject to a statistically significant level when measured by F-test.

Such a composition, wherein the composition comprises between 2.5 grams to 10 grams of fructo-oligosaccharide.

Such a composition, wherein the fructo-oligosaccharide composition comprises about 40-50% 1-kestose(GF2), 40-50% nystose (GF3) and 5-10% fructofuranosyl nystose (GF4).

Such a composition, wherein the fructo-oligosaccharide composition is in the form of a liquid or a solid dosage form for oral administration.

Such a composition, wherein the fructo-oligosaccharide composition further comprising other components selected from a group comprising galacto-oligosaccharides, vitamins, minerals, plant extracts, pharmaceutically acceptable excipients or a mixture therefore.

We claim:

1. A method of increasing relative abundance of *Oscillospira* in gastro-intestinal tract of a subject, the method comprising orally administering to said subject at least 2.5 grams per day of fructo-oligosaccharide, measuring the relative abundance of *Oscillospira*, and performing F-test to show significant increase in relative abundance of *Oscillospira* after administration of the fructo-oligosaccharide.

2. The method as claimed in claim 1, wherein 2.5 grams per day to 10 grams per day of fructo-oligosaccharide is administered to said subject.

3. The method as claimed in claim 1, wherein the subject is a mammal and preferably the subject is a human being.

4. The method as claimed in claim 1, wherein the fructo-oligosaccharide is administered for 1 day to 90 days.

5. The method as claimed in claim 1, wherein the fructo-oligosaccharide administered comprise about 40-50% 1-kestose(GF2), 40-50% nystose(GF3) and 5-10% fructofuranosylnystose (GF4) by weight.

6. The method as claimed in claim 1, wherein the subject is a human being.

* * * * *

UNITED STATES PATENT AND TRADEMARK OFFICE
CERTIFICATE OF CORRECTION

PATENT NO. : 10,874,680 B2
APPLICATION NO. : 16/140593
DATED : December 29, 2020
INVENTOR(S) : Anirban Bhaduri et al.

It is certified that error appears in the above-identified patent and that said Letters Patent is hereby corrected as shown below:

In the Claims

Column 7, Lines 12-13, Claim 3, "The method as claimed in claim 1, wherein the subject is a mammal and preferably the subject is a human being." should be --The method as claimed in claim 1, wherein the subject is a mammal.--.

Column 7, Lines 16-17, Claim 5, "The method as claimed in claim 1, wherein the fructo-oligosaccharide administered comprise about 40-50%" should be --The method as claimed in claim 1, wherein the fructo-oligosaccharide administered comprises about 40-50%--.

Signed and Sealed this
Second Day of March, 2021

Drew Hirshfeld
*Performing the Functions and Duties of the*
*Under Secretary of Commerce for Intellectual Property and*
*Director of the United States Patent and Trademark Office*